(12) United States Patent
Jewett

(10) Patent No.: US 11,724,067 B2
(45) Date of Patent: Aug. 15, 2023

(54) EVERSIBLE CATHETER WITH MINIMAL RUBBING FRICTION

(71) Applicant: Scott Jewett, Irvine, CA (US)

(72) Inventor: Scott Jewett, Irvine, CA (US)

( * ) Notice: Subject to any disclaimer, the term of this patent is extended or adjusted under 35 U.S.C. 154(b) by 218 days.

(21) Appl. No.: 17/175,568

(22) Filed: Feb. 12, 2021

(65) Prior Publication Data

US 2021/0252255 A1    Aug. 19, 2021

Related U.S. Application Data

(60) Provisional application No. 62/976,274, filed on Feb. 13, 2020.

(51) Int. Cl.
*A61M 25/01* (2006.01)
*A61M 25/00* (2006.01)

(52) U.S. Cl.
CPC ...... *A61M 25/0119* (2013.01); *A61M 25/007* (2013.01); *A61M 25/0017* (2013.01);
(Continued)

(58) Field of Classification Search
CPC .............. A61M 25/0119; A61M 25/00; A61M 25/0169; A61M 2025/0175
See application file for complete search history.

(56) References Cited

U.S. PATENT DOCUMENTS

| 5,846,259 A | 12/1998 | Berthiaume |
| 6,578,577 B2 | 6/2003 | Bonadio et al. |

(Continued)

FOREIGN PATENT DOCUMENTS

| EP | 1039149 | 9/2000 |
| EP | 1709987 | 12/2009 |

(Continued)

OTHER PUBLICATIONS

Mishra, Sujnanendra, "Tragedy of Inappropriately Managed Foley Catheter", Journal of Obstetrics and Gynaecology of India, Springer India, Oct. 2016, www.ncbi.nlm.nih.gov/pmc/articles/PMC5080259/.

(Continued)

*Primary Examiner* — Benjamin J Klein
*Assistant Examiner* — Katherine-Ph Minh Pham
(74) *Attorney, Agent, or Firm* — One LLP

(57) ABSTRACT

A flexible, polymer sleeve is provided that is everted into a body passageway in such a manner as to exert minimal rubbing friction on the internal walls of such passageway. The sleeve is housed within a tube assembly comprising a posterior tube that telescopingly slides into an insertion tube. The sleeve everts over the insertion tube, upon forward pressure applied thereon, as it extends forward into a body passageway, and consequently, causes the posterior tube to retract into the insertion tube. Multiple tubes can be telescoped to support the polymer sleeve and to keep a passageway open for the expelling of urine or body fluids, the insertion of tools, sanitation/antibacterial substances, or for the flow of liquids through the sleeve. The insertion tube can be locked in reference to the sleeve to prevent unintended removal of catheter assembly. Sleeve and tubing are removed by reversing the insertion and eversion movements.

7 Claims, 7 Drawing Sheets

(52) U.S. Cl.
CPC . *A61M 25/0147* (2013.01); *A61M 2025/0025* (2013.01); *A61M 2025/0175* (2013.01); *A61M 2205/0205* (2013.01)

(56) References Cited

U.S. PATENT DOCUMENTS

| | | | |
|---|---|---|---|
| 7,137,993 B2 | 11/2006 | Acosta et al. | |
| 7,195,615 B2 | 3/2007 | Tan | |
| 7,967,798 B2 * | 6/2011 | Reydel | A61M 25/0119 606/108 |
| 8,460,178 B2 | 6/2013 | Kumar et al. | |
| 8,781,601 B2 * | 7/2014 | Cully | A61N 1/0587 607/116 |
| 9,033,867 B2 | 5/2015 | Ziegler et al. | |
| D769,551 S | 10/2016 | Jennings et al. | |
| 10,420,454 B2 | 9/2019 | Lichtenstein | |
| 2002/0072732 A1 * | 6/2002 | Jung, Jr. | A61N 5/1002 604/535 |
| 2003/0114803 A1 | 6/2003 | Lerner | |
| 2004/0243144 A1 | 12/2004 | Bonadio et al. | |
| 2005/0027236 A1 | 2/2005 | Douk | |
| 2009/0043159 A1 | 2/2009 | Dumot | |
| 2019/0143078 A1 | 5/2019 | Tierney et al. | |

FOREIGN PATENT DOCUMENTS

| | | |
|---|---|---|
| WO | 2001072366 | 10/2001 |
| WO | 2020153860 | 7/2020 |
| WO | WO 2020/153860 A1 | 7/2020 |

OTHER PUBLICATIONS

WO, PCT/US21/18043 ISR and Written Opinion, dated Apr. 23, 2021.

* cited by examiner

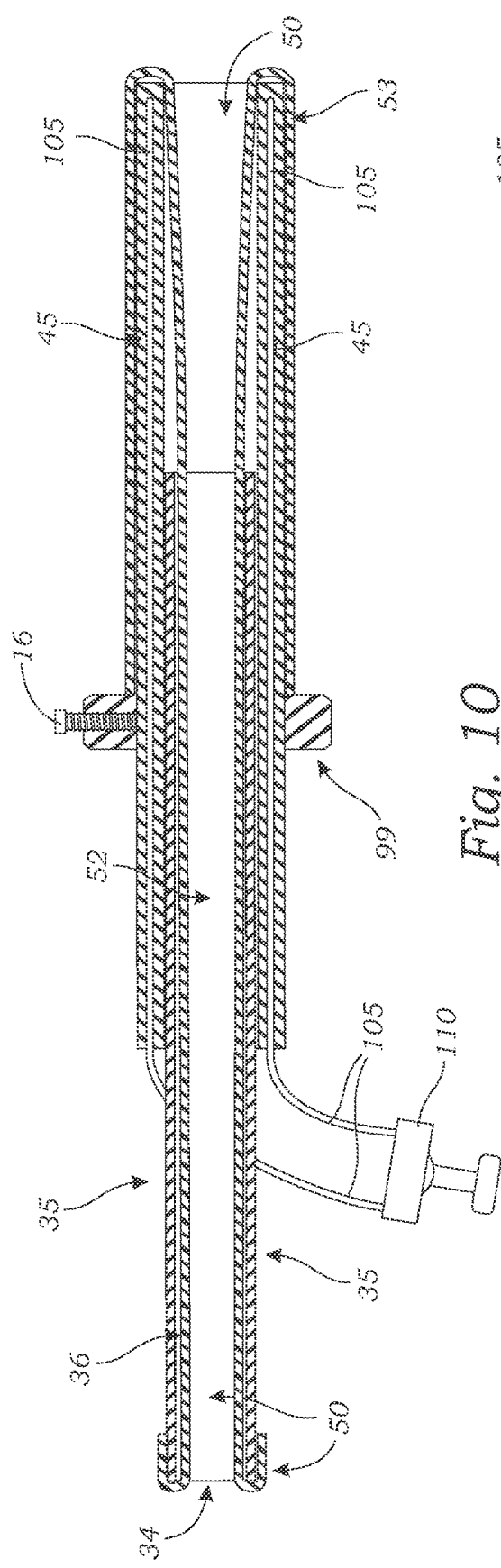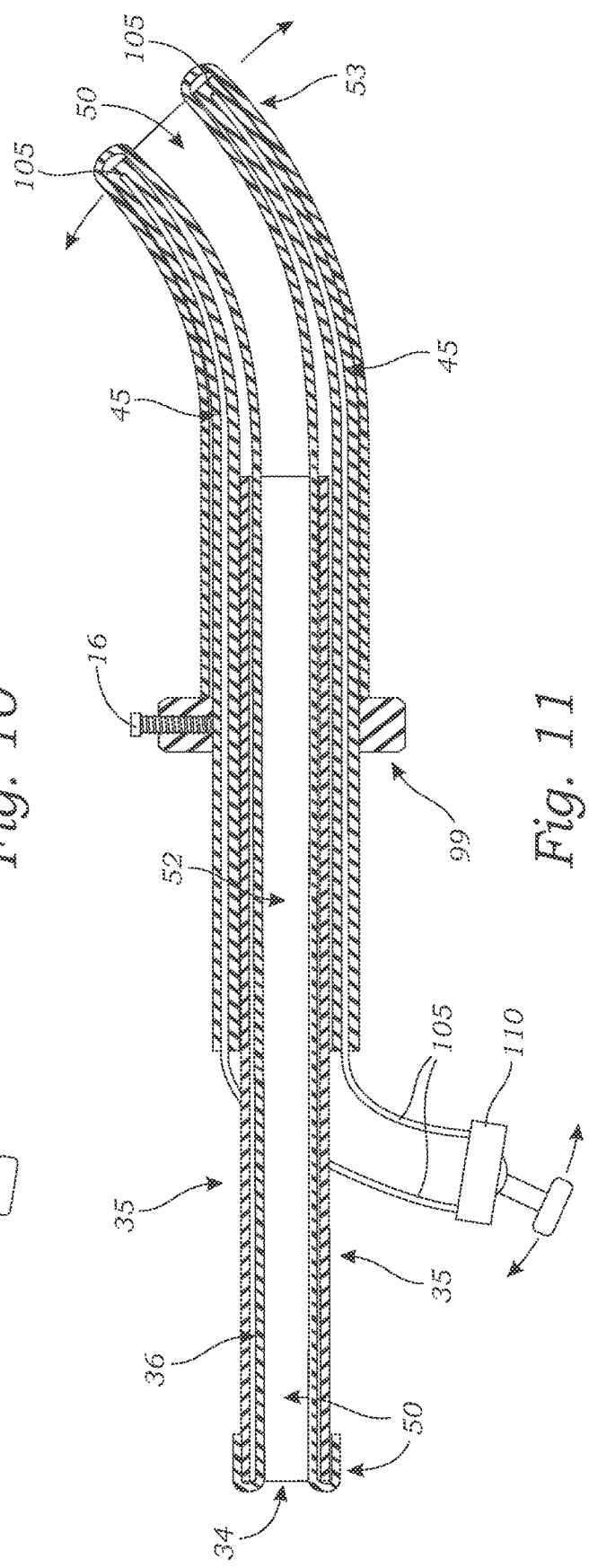

EVERSIBLE CATHETER WITH MINIMAL RUBBING FRICTION

RELATED APPLICATIONS

The present application claims benefit of U.S. Provisional Patent Application Ser. No. 62/976,274 filed on Feb. 13, 2020.

BACKGROUND OF THE INVENTION

The present invention relates to medical devices, more particularly the present invention relates to catheters introduced into body lumens.

Catheters are medical devices known for administering fluids within cavities, ducts, and vessels of a body. Additionally, catheters can introduce medical instruments or tools, such as endoscopes or stents, into the body of a patient. Catheters often must advance through tortuous and delicate passageways within a patient's body. Though catheters are commonly administered to patients who are anesthetized and asleep, often times they are inserted into patients who are conscious. Conscious individuals are therefore susceptible to pain and discomfort associated with the catheter insertion process, and because of this, can make it difficult for the administrator to properly place the catheter into the patient's body.

It is also common for catheters to be left within a patient's body for long, continuous periods of time. Urinary catheters, such as Foley catheters, for example, can remain in the urethra for several weeks, presenting general pain and discomfort to the patient. Such pain and discomfort may be compounded when the patient moves. Foley catheters are anchored and stabilized by an inflatable balloon located at the catheter's tip. Despite this, minimal movement by the patient may still result in irritating friction generating movement of the catheter rubbing against the urethra, thereby further exacerbating patient discomfort.

Notwithstanding the efforts of medical device manufacturers to reduce the coefficient of friction for their catheters, especially those intended for long-term wear, or introduction through a sphincter or narrow body lumen, patients frequently encounter trauma to sensitive tissues or discomfort associated with the insertion and manipulation of such catheters within the body. Irritation and discomfort may also be experienced with the catheter removal process.

Lubricants and lubricious polymers or other coatings can reduce these effects, but not always to a sufficient degree. Further, lubricant coating can be unfavorable due to its potential to inadvertently slip or dry. In the biliary system, for example, passing a biliary catheter through the ampulla of Vater and into the common bile duct very often results in swelling and subsequent closure of the opening, compromising normal drainage and making subsequent access difficult. Similar problems with discomfort or edema can be experienced by the patients when other anatomical sites are being accessed, for example, in the nasal passages, urethra, rectum, etc. While patient comfort may not be an issue when navigating internally such as within the biliary tree, the introduced device may be difficult or even impossible to advance from frictional forces acting against it, especially since these obstructions and narrowed passages often cannot be adequately visualized.

Additionally, as catheters are inserted into cavities, such as the urinary tract, venous or arterial vessels, they may pick up bacteria or other microbes which can adhere to the catheter surface and colonize, thereby presenting a significant threat of infection to the patient. Traditional catheters can cause the transportation of these bacteria, viruses, microbes, or other contaminants from one portion of the passageway to another as the catheter is slid into position, effectively spreading these from infected areas to sanitary areas, worsening the problem. Microbial growth is especially common in catheters intended for long-term wear. Moreover, catheters, that utilize balloons, such as Foley catheters, provide additional surface area for pathogens to track up and produce a biofilm around, thereby creating more opportunity for infection to ensue.

Furthermore, additional complications, such as deflation and rupture, are associated with catheters utilizing inflation mechanisms. For instance, the balloon may be filled with a substance, such as saline, which can begin to precipitate and crystalize, thereby hardening the balloon and complicating the removal of the catheter from the patient's body. Additionally, the fluid-filled balloon may puncture or leak, leaving pieces of broken catheter material within the patient's body. A malfunctioning balloon can lead to patient injury, pain, discomfort, and sometimes even death.

Thus, it would be desirable to a have a catheter apparatus that utilizes tubes telescopically connected to advance an eversible sleeve through body lumen. Such an embodiment would minimize rubbing friction by providing a gliding surface for the eversible catheter to unfurl across, thereby providing a less irritable and traumatic experience for the patient, and smoother catherization for the administrator. The unfurling of the sleeve from inside the catheter, around the tip, to the outside of the catheter insertion tube can effectively pull or walk tissue and/or blockages out of the way with less "pushing" trauma to said tissue or blockage.

It would also be desirable to have a catheter apparatus having an eversible sleeve housed within an internal cavity of a telescoping tube. Advantageously, a sanitizing or antibacterial substance can be dispensed onto a pre-everted portion of the sleeve so as to apply medicine onto sleeve as it everts into body lumen. This catheter embodiment would minimize user contact and exposure to pathogens with the indwelling device so as facilitate safer and more sterile use.

It would further be advantageous to have an eversible catheter that utilizes a constricting collar as a locking mechanism so as to prevent the incidence of user error and the many complications associated with inflated anchors or stabilizers.

SUMMARY OF THE INVENTION

Briefly in accordance with the invention, an improved catheter assembly is provided which includes an eversible sleeve construction. The catheter assembly includes a thin, eversible sleeve as a catheter that would otherwise be difficult to insert. In addition, the catheter assembly includes a tube assembly comprising one or more tubes for inserting the eversible sleeve into a narrow body lumen. In the preferred embodiment, the tube assembly comprises two flexible, open-ended tubes in which one tube telescopically slides within the other.

Preferably, the telescoping tube assembly comprises an insertion tube and a posterior tube. Even more preferably, the posterior tube's external diameter is smaller than the insertion tube's internal diameter such that the posterior tube can retract into insertion tube upon the user applying forward exertion onto the posterior tube. Initially, a majority of the sleeve is housed within the tube assembly in a retracted configuration. Specifically, the sleeve lines both the internal chambers of the posterior tube and insertion tube, while a pre-everted portion of the sleeve remains on the insertion tube's external surface, wherein it covers the tube's proximal end and forms an insertion tip.

The sleeve can be contiguous from the proximal end of the insertion tube to the distal end of the posterior tube, thereby creating a hermetically sealed conduit. The insertion tube and posterior tube are used to insert and evert the sleeve, and to hold the sleeve open to create a catheter conduit. To insert the catheter into a body lumen, the tube assembly is positioned adjacent to and distal relative to a body lumen's opening. Specifically, as the insertion tube is pushed inward into the lumen, the eversion of the sleeve will pull on the posterior tube so as to retract it into the posterior tube, thereby telescoping the posterior tube into the insertion tube. The insertion tube is consequently extended into the body lumen of the patient by pushing the insertion tube into the lumen, in a similar fashion as inserting a traditional catheter. Even more specifically, and contemporaneously with the forward movement of the telescoping tubes, the sleeve everts over the extended portion of the insertion tube so as to fully envelop its external surface as it enters the body lumen. Notably, the posterior tube moves into the insertion tube as the insertion tube enters the body lumen to insert and evert the sleeve into a body passageway. Preferably, the sleeve is attached to the distal end of the posterior tube so that the posterior tube is pulled forward as the sleeve everts forward past the insertion tip and is inserted into the body passageway.

Additionally, a guiding mechanism is positioned so as to circumferentially surround the insertion tube's external surface wherein it functions as a stopper preventing inadvertent advancement of the tube assembly into the body lumen. Preferably, the guiding mechanism's body comprises a holding ring and a fastener. The holding ring is for the technician to grasp during catheter insertion and withdrawal and allows for more effective and precise guiding of the catheter assembly as it extends or retracts into and out of a given body passageway.

Preferably, the guiding mechanism includes a fastener that is either threaded through the holding ring or can be locked down against the insertion tube once the catheter is in its final desired position. In the fastener's locked position, it prevents the insertion tube from reversing and retracting from the eversion of the sleeve back into the inside of the insertion tube. Moreover, the fastener in its locked position helps anchor the sleeve in place once it is fully inserted by putting pressure between the sleeve and the insertion tube. In the preferred embodiment, the guiding mechanism can be a simple constricting collar. In an even more preferred embodiment, the collar may include a radially projecting body having a diameter sufficiently large so as to not inadvertently enter the body lumen and keep the initially distal end of the sleeve outside the body lumen.

Furthermore, the catheter can be removed from a body passageway by reversing the steps of the insertion process. Specifically, fastener must be configured to its unlocked position and the posterior tube is pulled distally relative to the insertion tube and body lumen. The withdrawal of the insertion tube then un-everts the sleeve from the passageway. After the insertion tube and sleeve are completely withdrawn from the body lumen, the catheter assembly can be disengaged from the lumen opening.

The sleeve need not have a low coefficient of static friction in relation to the inside of the body passageway or mucosal lining. In fact, a static or friction between the sleeve and passageway may be desirable in some circumstances, especially if a collar or the like is utilized. The coefficient of static friction between the inner surface of the body passageway and the sleeve will hold the system in place once the holding is locked in reference to the insertion tube. For some embodiments, it may be desirable to employ an increased static and/or kinetic coefficient of friction between the sleeve and body tissue by altering the material choice, the surface profile, or by adding an adhesive coating to the sleeve. Ideally, this friction acts to minimize slippage, but does not have a high peel resistance.

The sleeve may have low elongation to minimize rubbing friction. For alternative uses, the sleeve may stretch, and may be made of materials like latex.

In a preferred embodiment, a plurality of filaments or wires may radially nest within the telescoping tube assembly's internal chambers so as to cause the tip to bend in the direction desired. Specifically, a combination of the filaments or wires are pulled from the distal end of the posterior tube in order to bend the tip. Additionally, the filaments or wires may be attached to a control mechanism.

In yet another embodiment of the catheter assembly, the tube assembly comprises swivel joints so as to allow for bending and curved manipulation by a user.

Wired catheter assemblies may further include radial holes which circumferentially encompass the insertion tube's proximal end so as to provide for better maneuvering and trackability of the catheter assembly.

In some embodiments, a fluid collection bag can be attached to the distal end of the catheter assembly to collect drained fluid from a passageway. In other embodiments, the catheter assembly functions as an axis port for transporting medical instruments to an internal site within a body. In many embodiments, it is desirable to provide a catheter assembly that is sufficiently flexible so as to be capable of navigating tortuous paths within a body passageway. It is also desirable for the catheter assembly to be capable of small, precise manipulations to assume various complex curves within the body.

Advantageously, insertion of the catheter will not cause damage to the body lumen due to friction.

Also advantageously, a sanitizing or antibacterial substance can be applied to the exterior of the pre-everted section of the sleeve which then gets commuted to the inside surface of the urethra as the unfurling sleeve comes in contact with the sanitizing or antibacterial substance before entering the body.

Still an additional advantage is that the sleeve is not touched by human hands during catheter insertion, preventing contamination or the introduction of germs or bacteria into the body lumen.

BRIEF DESCRIPTION OF THE DRAWINGS

FIG. 10 is a perspective cutaway view of at least one embodiment of the insertion tube of the catheter assembly of FIG. 2, wherein the walls of the insertion tube comprise a plurality of wires or filaments; and FIG. 11 is a perspective cutaway view of the catheter assembly of FIG. 10 wherein the insertion tube's tip is in bent configuration;

DETAILED DESCRIPTION OF THE INVENTION

Figure 1:
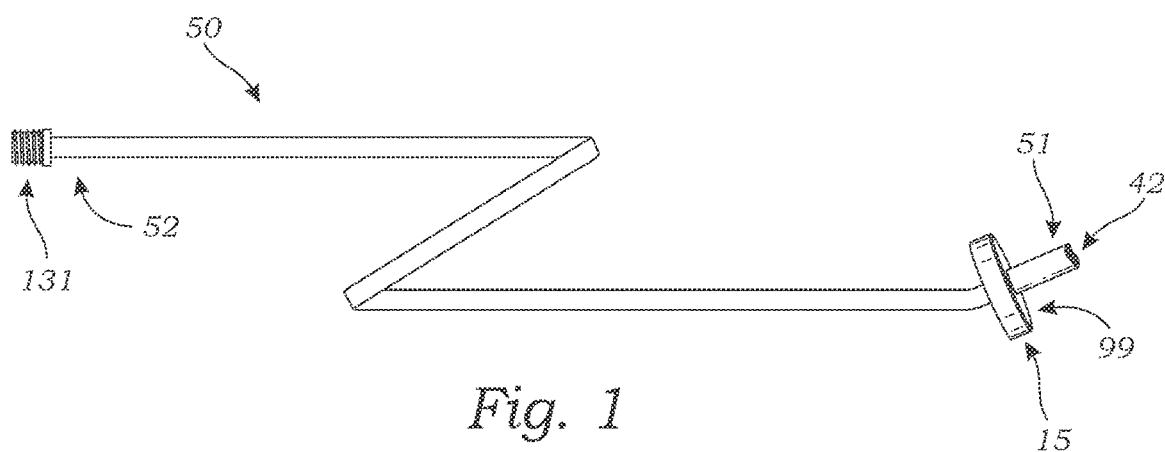
FIG. 1 is a longitudinal perspective view of the contiguous eversible sleeve illustrating its leading end proximate to a guiding mechanism and its trailing end proximate to removable fluid bag attachment.
Figure 2:
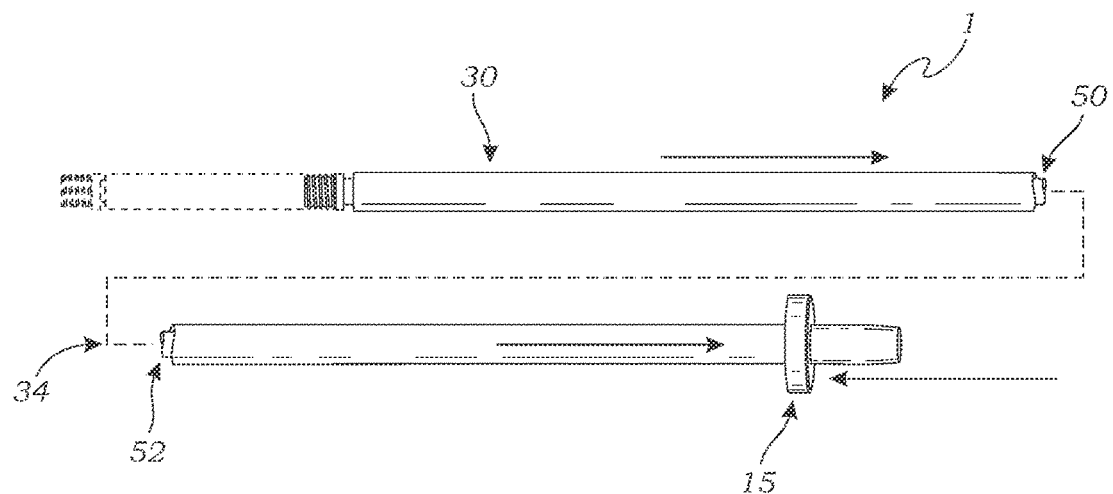
FIG. 2 is a longitudinal, side perspective view of the telescoping tube assembly, wherein the posterior tube is retracting into the insertion tube, illustrating the catheter assembly shifting to its fully extended configuration.
Figure 3:
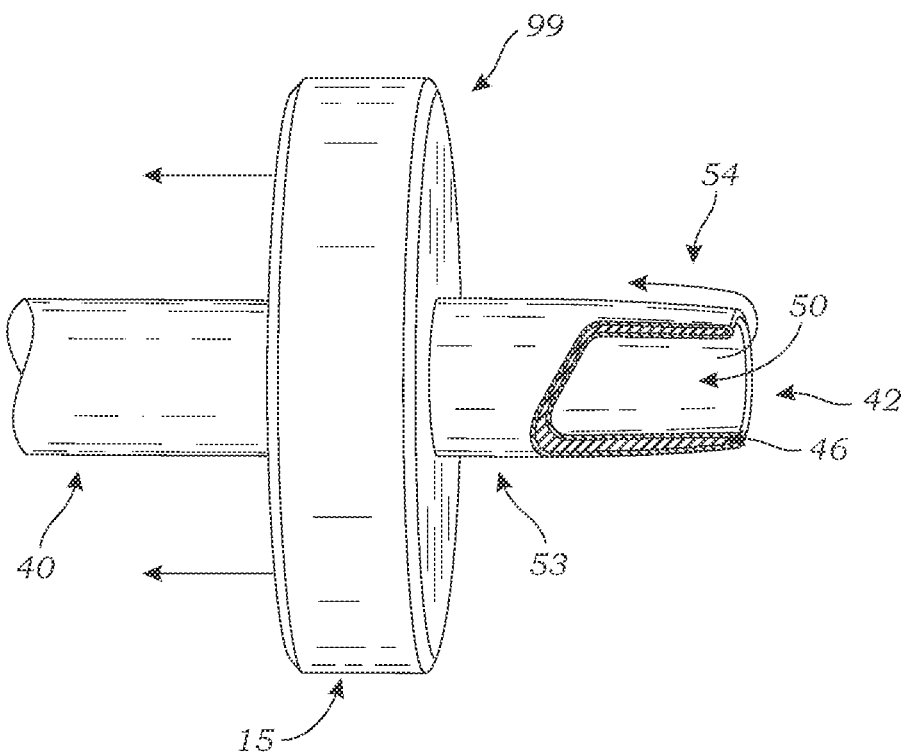
FIG. 3 is an enlarged, partially cutaway view of the proximal portion of the catheter assembly of FIG. 2 illustrating the eversible sleeve being pulled from the insertion tube's internal chamber and everted over the insertion tube's external surface.
Figure 4:
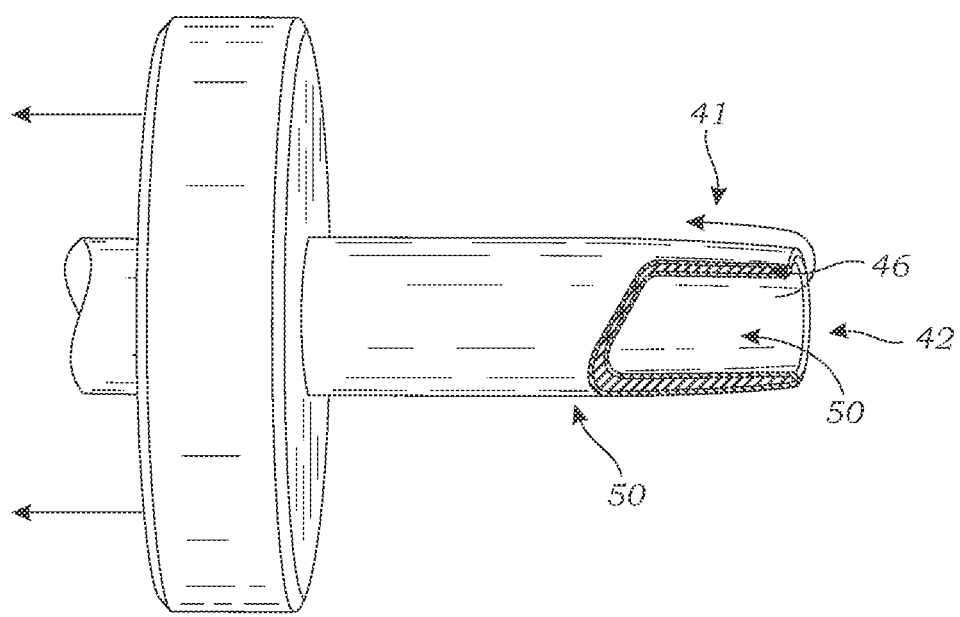
FIG. 4 is an enlarged, partially cutaway view of the proximal portion of the catheter assembly of FIG. 2 in a more extended configuration than FIG. 3, wherein the eversible sleeve is everting over the external surface of the insertion tube as the insertion tube is being extended in a proximal direction.
Figure 5:
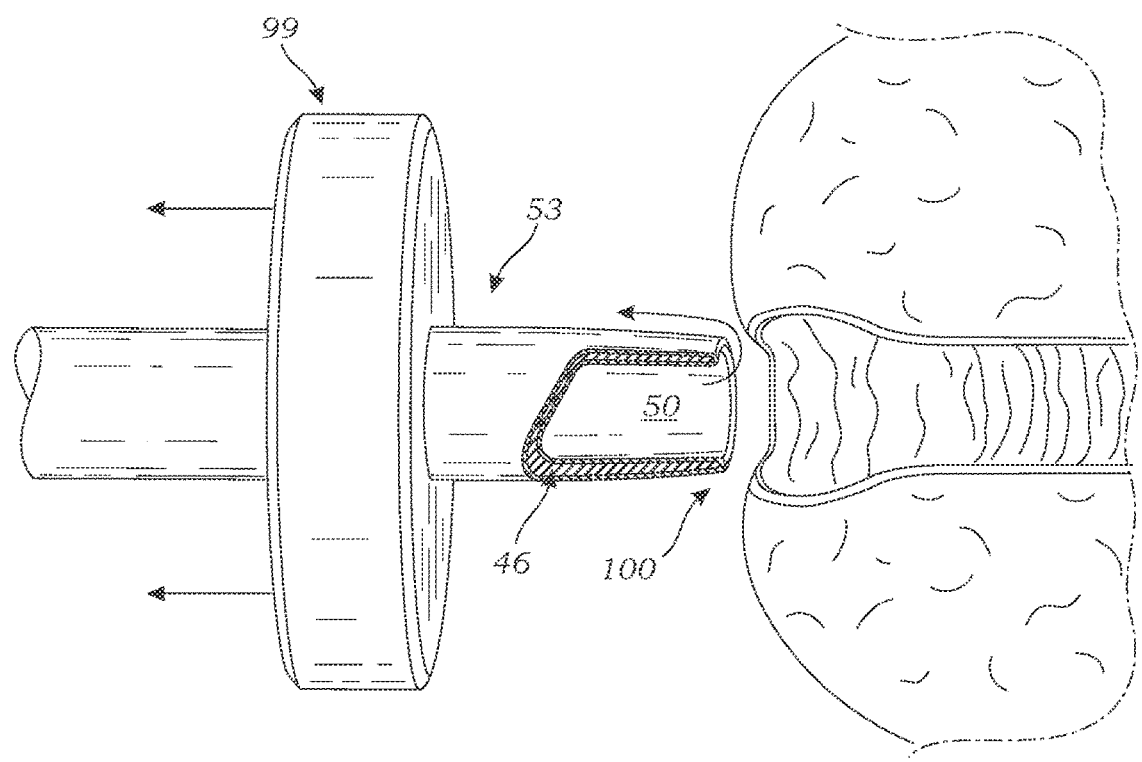
FIG. 5 is an enlarged, partially cutaway view of the proximal portion of the catheter assembly in FIG. 2 illustrating the catheter assembly being inserted into a body passageway wherein the eversible sleeve is everting over the insertion tube's external surface near the insertion tip.
Figure 6:
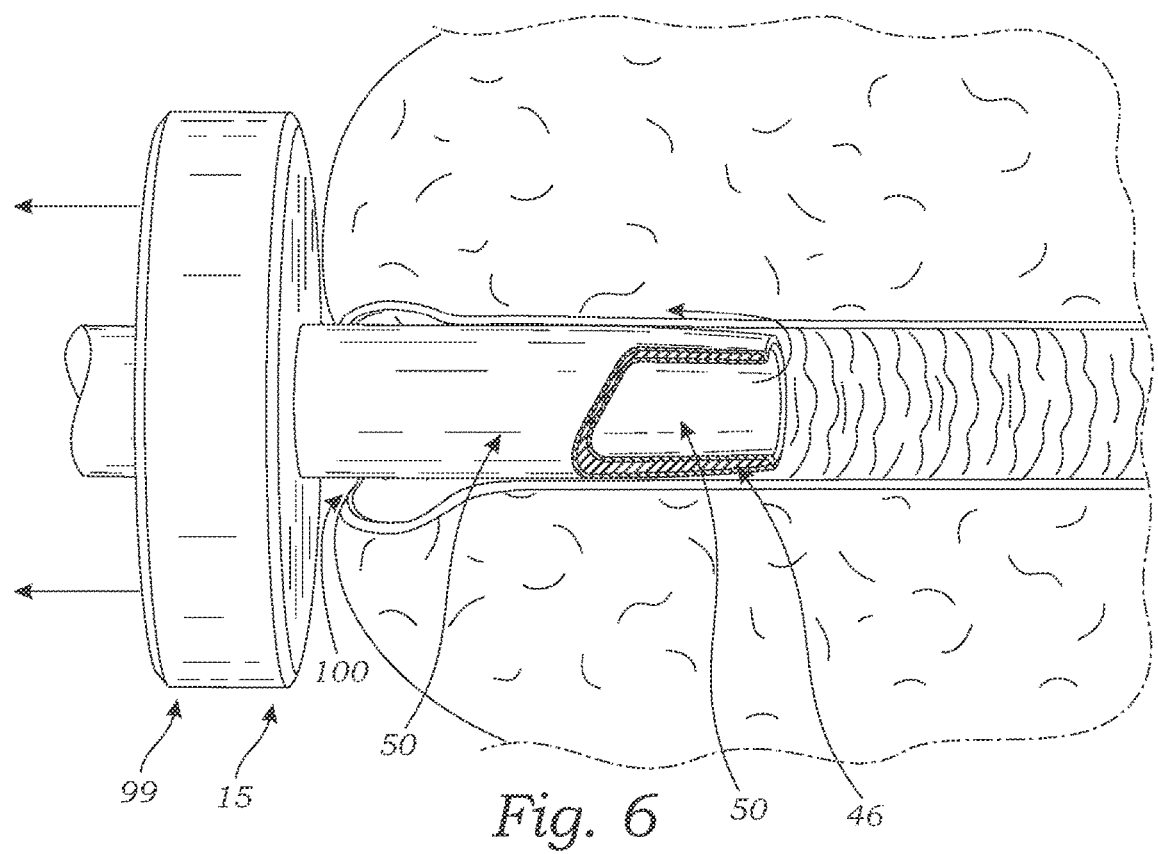
FIG. 6 is an enlarged, partially cutaway view of the proximal portion of the catheter assembly in FIG. 2 illustrating the catheter assembly inserted into a body passageway, wherein the eversible sleeve has enveloped the extended portion of the insertion tube's external surface so as to create a barrier between the external surface and the internal surface of the body passageway and the guiding mechanism remains outside of the body passageway.

While the present invention is susceptible of embodiment in various forms, as shown in the drawings, hereinafter will be described the presently preferred embodiments of the invention with the understanding that the present disclosure is to be considered as an exemplification of the invention, and it is not intended to limit the invention to the specific embodiments illustrated.

With reference to FIGS. 1-9, the catheter of the present invention is illustrated as a catheter assembly 1 which includes three primary components: a telescoping tube assembly 20, an eversible sleeve 50, and a guiding mechanism 99. In addition, the catheter assembly 1 may include a fluid collection bag attachment 131 that collects drained fluids from the catheterized body passageway 100.

The telescoping tube assembly 20 includes one or more telescopically connected tubes. Preferably, the tube assembly 20 comprises two telescopic tubes: a posterior tube 30 and an insertion tube 40, both of which are formed of flexible material and open-ended on each annular end. As illustrated in FIGS. 2-3, 8 and 10, the posterior tube 30 includes a proximal end 31, a distal end 33, an external surface 35, and an internal chamber 36 extending throughout its hollow interior annular space so as to be defined by the posterior tube's proximal end 31 and distal end 33. The posterior tube's proximal end 31 forms a proximal opening 32, and the posterior tube's distal end 33 forms a distal opening 34.

Figure 7:
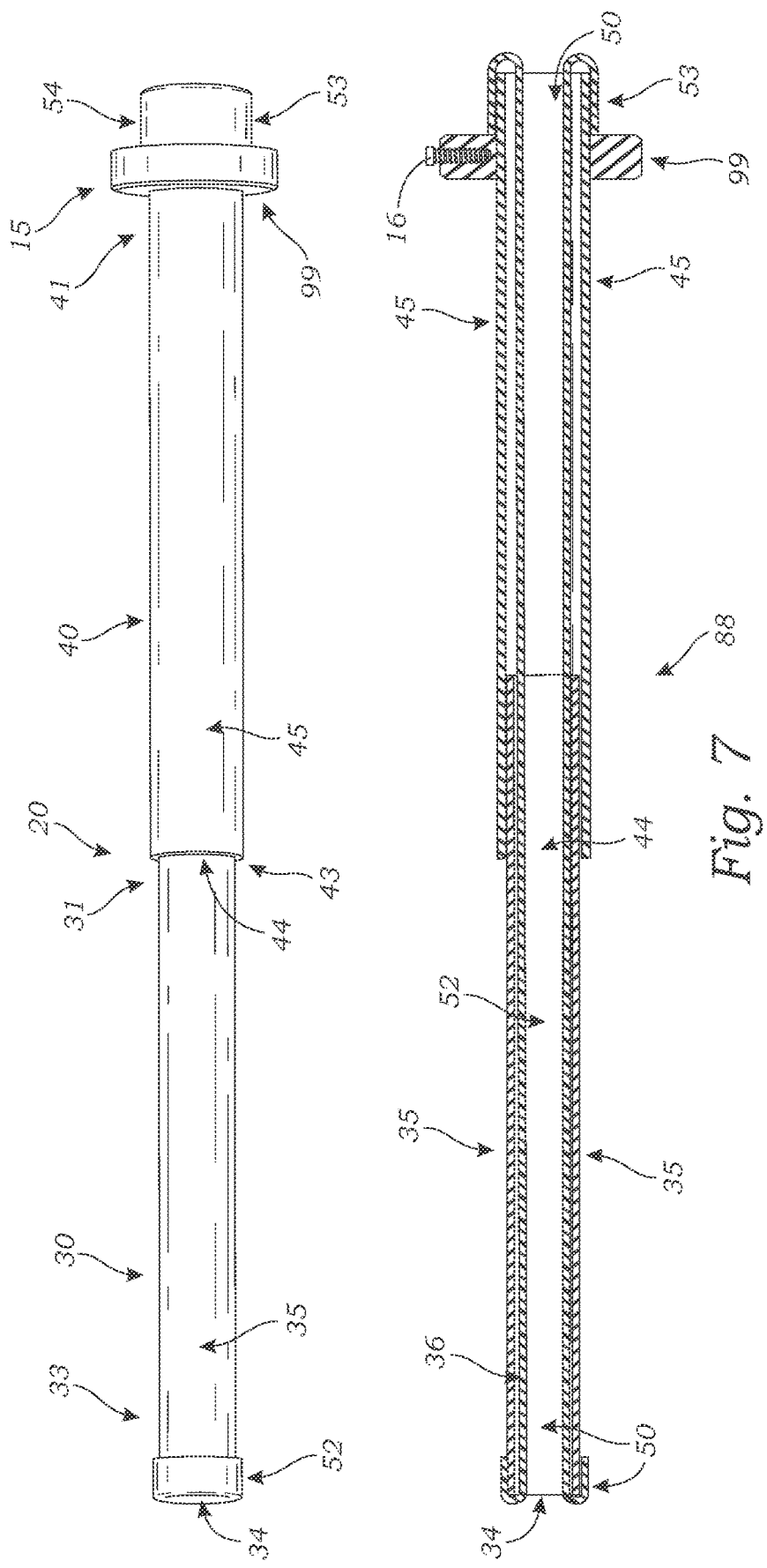
FIG. 7 is longitudinal, side perspective view and a longitudinal cutaway view of the catheter assembly of FIG. 2, illustrating the catheter assembly in its fully retracted configuration prior to insertion into a body passageway.
Figure 8:
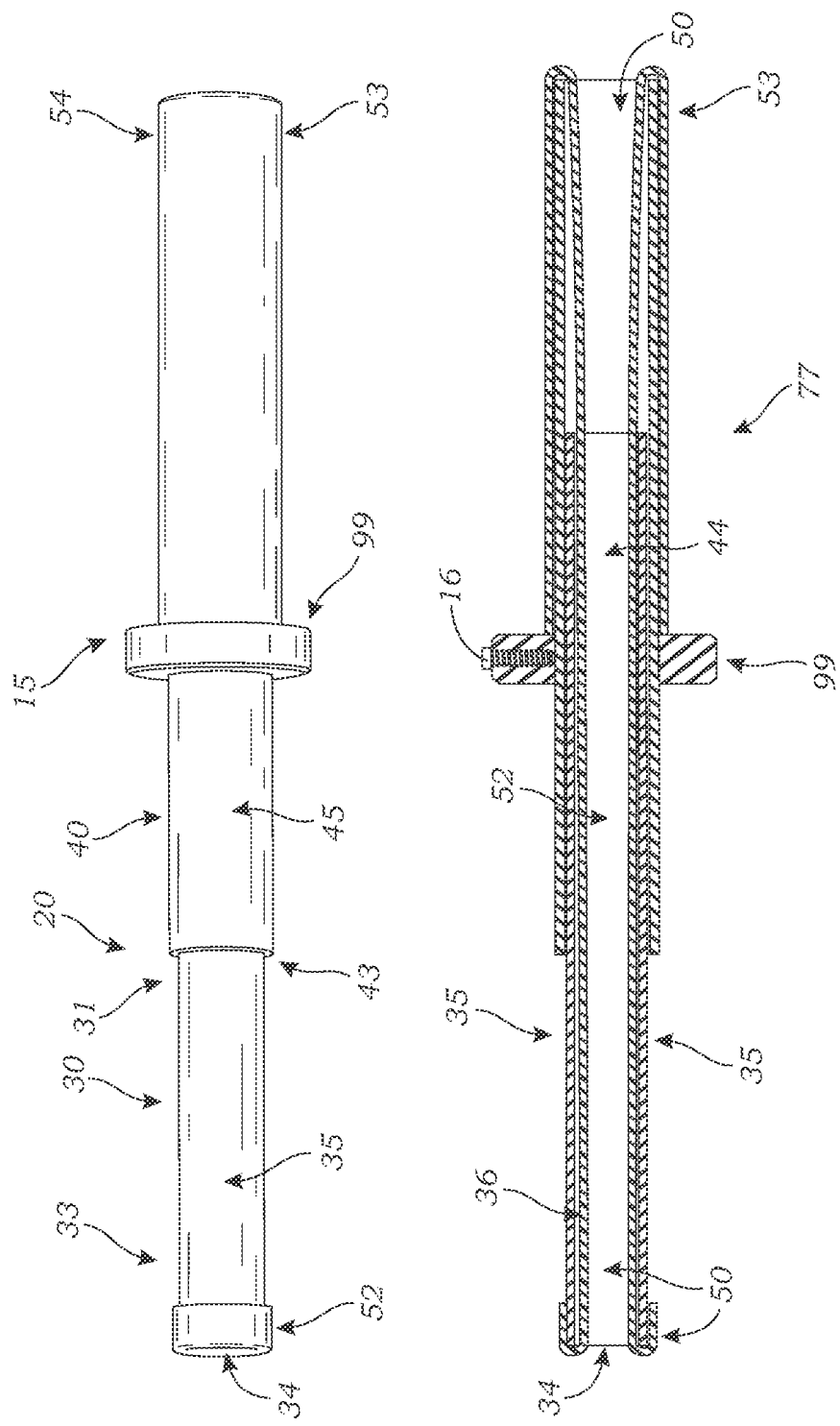
FIG. 8 is a longitudinal, side perspective view and a longitudinal cutaway view of the catheter assembly illustrated in FIG. 2, illustrating the catheter assembly in its fully extended configuration as it is fully inserted into a body passageway.
Figure 9:
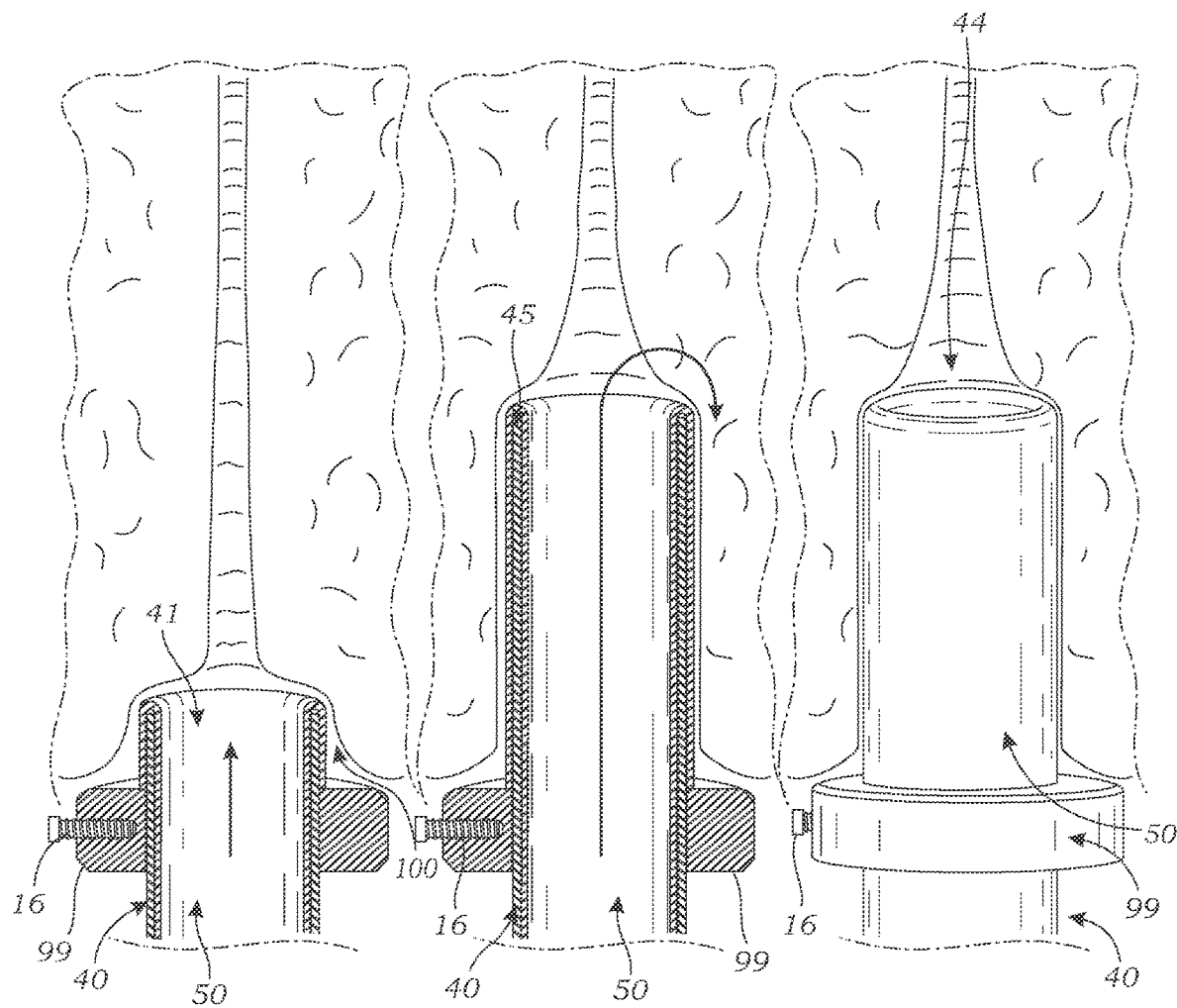
FIG. 9 is a schematic view of the catheter assembly of FIG. 2, illustrating a cutaway view of the insertion tube positioned adjacent to a body passageway prior to insertion, a cutaway view of the insertion tube being extended into the body passageway, and a perspective view of the eversible sleeve everting over the portion of the insertion tube that has extended into the body passageway.

As illustrated in FIGS. 7 and 8, the insertion tube 40 includes a proximal end 41, a distal end 43, an external surface 45, and an internal chamber 46 extending throughout its hollow interior annular space so as to be defined by the insertion tube's proximal end 41 and distal end 43. The insertion tube's proximal end 41 forms a proximal opening 42, and the outer telescoping tube's distal end 43 forms a distal opening 44.

Preferably, the posterior tube 30 has an external diameter sized to correspondingly collapse, or telescopically slide, into the insertion tube 40. Additionally, the insertion tube 40 has an internal diameter sized for receipt of the slidably advancing posterior tube 30. In some embodiments, the telescoping tube assembly 20 comprises an inner wall 2 embedded with wires or filaments 105 so as to provide structural reinforcement and flexibility for the catheter assembly 1.

As illustrated in FIGS. 2-11, the tubes' assembly is arranged in the following manner: the insertion tube's proximal end 41 is positioned adjacent to a body passageway's opening, the posterior tube's proximal end 31 is telescopically connected to and housed within the insertion tube 40 near the insertion tube's distal end 43, and the posterior tube's distal end 33 is positioned farthest from the body passageway's opening and configured so that a fluid collection bag attachment 131 may be affixed thereto.

As illustrated in FIGS. 1-11, a majority of the eversible sleeve 50 is initially housed within the telescoping tube assembly 20, lining the surface of posterior tube's internal chamber 36 and the insertion tube's internal chamber 46. The eversible sleeve 50 extends therein from the insertion tube's proximal opening 32 to the posterior tube's distal opening 34, thereby forming a contiguous and hermetically sealed conduit within the telescoping tube assembly 20. Additionally, if a collection bag attachment 131 is affixed to the trailing end 52 and the posterior tube's distal end 33, the bag attachment 131 is contiguous and in fluid connection with the hermetically sealed conduit.

A majority of the eversible sleeve 50 is initially maintained within the telescoping tube assembly 20 in a retracted configuration, and a portion of the eversible sleeve is pre-everted and initially resides on the insertion tube's external surface 45 at its proximal end 41. The pre-everted portion 53 thereby forms an insertion tip 54. Upon forward advancement of the insertion tube 40 into the body lumen, and consequently, the eversion of the sleeve, the insertion tip is extended forward so as to form the most proximal tip of the catheter assembly entering the body passageway. In a preferred embodiment, a sanitizing substance or antibacterial may be applied to the eversible sleeve 50 housed within the telescoping tube assembly 20, thereby dispersing said substance to the inside of the lumen or passageway as the sleeve 50 everts and makes contact with the inside surface of the lumen or passageway. The exterior of the of the eversible sleeve 50 should have a low coefficient of friction between the sleeve 50 and the insertion tube's internal chamber 46. Additionally, a lubricant can be added so as to assure that the eversible sleeve 50 slides easily around the insertion tip 54 while unfurling into the body passageway 100.

As best illustrated in FIG. 1, the eversible sleeve 50 comprises a leading end 51 and a trailing end 52. The trailing end 52 is affixed to the posterior tube's distal end 33 so as to cause the posterior tube 30 to be pulled forward into the insertion tube's internal chamber 46 when the eversible sleeve 50 is everted into the intended body passageway 100. Moreover, the leading end 51 is proximal to and immediately adjacent to a guiding mechanism 99 near the insertion tube's proximal end 41, and in response to eversion of the sleeve 50, the insertion tube's proximal end 41 is pushed forward so as to advance into the body passageway 100. At the same time and in response to the forward advancement of the tubes, the eversible sleeve 50 unfurls over the extended portion of the insertion tube 40.

In the telescoping tube assembly's fully extended configuration 88, the posterior tube's proximal end 31 partially resides within the insertion tube's internal chamber 46. In the telescoping tube assembly's full retracted configuration 77, the insertion tube 40 is fully inserted within the intended body passageway 100 and the eversible sleeve 50 has unfurled to envelop the insertion tube's extended external surface 45 so as to create a barrier between the insertion tube 40 and the body lumen 100.

In the preferred embodiment, the insertion tube 40 has a length equal to at least 1 L, the posterior tube 30 has a length equal to at least 1 L, and the eversible sleeve 50 has a length equal to at least the combined length of the insertion tube 40 and the posterior tube 30.

The eversible sleeve 50 unfurls at a length directly dependent on and proportional to the length of insertion tube's 40 extended portion. Conversely, upon withdrawal of the telescoping tube assembly 20, the eversible sleeve 50 retracts at a length directly dependent on and proportional to the length of the insertion tube 40 that is withdrawing from the body lumen 100.

Preferably, the eversible sleeve 50 is pliant but not stretchy. Even more preferably, the eversible sleeve 50 is formed of thin, flexible polymer film that provides low lateral elongation potential so as to minimize rubbing friction between the sleeve 50 and internal walls of the body lumen. The sleeve 50 should have a low coefficient of static friction with insertion tube's internal chamber 46, the insertion tip 54, and the insertion tube's external surface 46 so as to reduce frictional resistance therebetween to provide a smooth gliding surface in the tube assembly 20. A low coefficient of friction may be accomplished by altering the material choice, surface profile, or by adding a lubricant coating to the sleeve 50.

Additionally, the sleeve 50 need not have a low coefficient of static friction in relation to the inside of the intended body passageway 100. In fact, a static or friction between the sleeve 50 and passageway 100 may be desirable in some circumstances. The coefficient of static friction between the internal surface of the body passageway 100 and the sleeve 50 will hold the system in place. For some embodiments, it may be desirable to employ an increased static and/or kinetic coefficient of friction between the sleeve 50 and body tissue by altering the material choice, the surface profile, or by adding an adhesive coating to the sleeve 50. Ideally, this friction acts to stabilize the inserted catheter assembly 1 and minimize slippage, but it should not have a high peel resistance.

The catheter assembly 1 also comprises a guiding mechanism 99 that slidably engages the insertion tube's external surface 45, attached to the pre-everted portion 54. Specifically, the guiding mechanism 99 comprises a holding ring 15 and a fastener 16, such as a set screw or compression pin 16. Preferably, the holding ring 15 is a collar circumferentially surrounding the insertion tube's external surface 45 and has a radially projecting body having a diameter sufficiently sized to prevent the guiding mechanism 99 from entering the body lumen 100. Preferably, the holding ring 15 includes a gripping surface whereby the technician can grasp the telescoping tube assembly 20 by during catheter insertion. The holding ring 15 allows for more effective and precise guiding of the catheter assembly 1 as it extends into or retracts out of a given body passageway 100.

Preferably, the guiding mechanism 99 includes a fastener 16, such as a set screw or pin. The fastener 16 resides on the upper portion of the holding ring 15 and can threadably engages the holding ring 15 and insertion tube 40. Even more preferably, the fastener 16 has two configurations: a locked position and an unlocked position. In the locked position, the fastener 16 is threaded into the holding ring 15 and insertion tube 40, so as to apply pressure between the eversible sleeve 50 and insertion tube 40.

Thus, the fastener 16, functions as a stopper by preventing the insertion tube 40 and sleeve 50 from further forward advancement. Additionally, the fastener 16 in its locked position prevents the posterior tube's distal end 33 and the sleeve's trailing end 52 from pulling out during the catheterization process, and the posterior tube 30 from sliding out of the insertion tube 40. In this way, the fastener 16 locks the telescoping tube assembly 20 in place and longitudinally defines the maximum length of the telescoping tube assembly's fully retracted configuration 77.

In the fastener's 16 unlocked position, the fastener is unthreaded from the holding ring 15 and insertion tube 40, thereby allowing the technician to proceed with withdrawing the catheter assembly 1 from the body passageway 100.

Specifically, and as illustrated in FIGS. 2-11, to insert the catheter assembly 1 into a body passageway 100, the telescoping tube assembly 20 is positioned adjacent to and distal relative to the body passageway 100. The technician holds onto holding ring 15 and applies forward pressure onto the insertion tube 40, thereby pulling the posterior tube 30 into the insertion tube 40. Contemporaneously, the sleeve 50 everts over the extended portion of the insertion tube's external surface 45 so as to fully envelop the insertion tube 40 as it is inserted into the body passageway 100. Once the tube assembly 20 has reached its fully retracted configuration 77, the technician then threads the fastener 16 into the holding ring 15 so as to lock against insertion tube 40, and thereby prevent further advancement or retraction of insertion tube 40 and sleeve 50.

Conversely, to withdraw the catheter assembly 1 from a body passageway 100, technician unthreads the fastener 16 from the holding ring 15 and insertion tube 40, so as to unlock the fastener 16. As the technician holds the insertion tube 40 and pulls the posterior tube 30 in a distal direction relative to the body lumen or passageway 100 the insertion tube 40 is retracted from the body lumen and the sleeve 50 is everted back into the inside of the catheter assembly 1. Correspondingly, and in response to the withdrawal of the insertion tube 40 from the body lumen 100, the eversible sleeve 50 un-everts and disengages from the body lumen 100 as it retracts back into the telescoping tube assembly 20.

In some embodiments of the catheter assembly 1, fluid is drained from the body passageway 100 and collected in a fluid collection bag 131. In other embodiments of the catheter assembly 1, the insertion tube's internal chamber 46 and the posterior tube's internal chamber 36 provide a port for allowing sampling and/or operative instruments to be transported along their axis to an internal site within the body. When the catheter assembly 1 functions as an axis port for medical tools, a pliable and highly maneuverable catheter assembly 1 is desirable.

In one embodiment of the catheter assembly 1, a plurality of filaments or wires 105 radially nest within the tube assembly's inner wall 2 so as to provide a steering mechanism for the catheter assembly 1 and allow the insertion tube's proximal end 41 to bend in the direction desired by the user. In this embodiment, the filaments or wires 105 may extend through the entire length of the telescoping tube assembly 20. Further, and in response to the user applying tensile force on the filaments or wires 105 at the posterior tube's 30 most distal end, the insertion tube's proximal end 41 will bend proportionally and in the direction of the force applied.

Preferably, this embodiment further comprises a plurality of radial holes circumferentially surrounding the insertion tube's proximal end 41. The radial holes, in combination with the filaments or wires 105, provide for more optimal and pliable maneuvering of the catheter assembly 1 instrument.

In yet another embodiment, the catheter assembly 1 may comprise filaments or wires 105, and swivel joints located proximate to the insertion tube's proximal end 41. The swivel joints allow the catheter assembly 1 to rotate about the filaments or wires 105, thereby allowing the insertion tube's proximal end 41 to bend.

More preferably, the insertion tube's proximal end 41 can be varied infinitely between about 0 degrees and 90 degrees in relation to the tube assembly's 20 longitudinal axis. Additionally, control mechanisms 110 may be utilized to control the tension and steering of the filaments or wires 105.

While several particular forms of the invention have been illustrated and described, it will be apparent that various modifications can be made without departing from the spirit and scope of the invention. Accordingly, it is not intended that the invention be limited except by the following claims.

The invention claimed is:

1. A telescoping tube assembly comprising:
   two or more telescoping tubes including a posterior tube slidable within an insertion tube;
   said posterior telescoping tube is formed of flexible material having a proximal end, a distal end, an external surface, and an internal chamber extending throughout its hollow annular space so as to be defined by said posterior tube's proximal end and said posterior tube's distal end, said posterior tube's proximal end forming a proximal opening, and said posterior tube's distal end forming a distal opening;
   said insertion tube formed of flexible material having a proximal end, a distal end, an external surface, and an internal chamber extending throughout its hollow annular space so as to be defined by said insertion tube's proximal end and said insertion tube's distal end, said insertion tube's proximal end forming a proximal opening, and said insertion tube's distal end forming a distal opening;
   said posterior tube having an external diameter sized to correspondingly collapse into said insertion tube, and said insertion tube having an internal diameter sized for receipt of slidably advancing posterior tube;
   a guiding mechanism having a holding ring, and said guiding mechanism slidably engaged and circumferentially surrounding the insertion tube's external surface;
   said holding ring having a radially projecting body, and said holding ring having a gripping surface for the technician to hold during catheterization and handling of said telescoping tube assembly;
   an eversible sleeve having a leading end and a trailing end, and formed of thin, flexible polymer material, said eversible sleeve lining the internal chamber of said posterior tube and the internal chamber of said insertion tube so as to create a contiguous and hermetically sealed conduit extending from said insertion tube's proximal opening to said posterior tube's distal opening;
   at least a portion of said eversible sleeve is initially maintained in a retracted configuration within said telescoping tube assembly, and said eversible sleeve includes a pre-everted portion covering said external surface of said insertion tube's proximal end so as to form an insertion tip;
   said eversible sleeve's trailing end is affixed to said posterior tube's distal end so as to cause said posterior tube to be pulled forward into said insertion tube's internal chamber when said eversible sleeve is pulled forward towards intended body passageway, said eversible sleeve's leading end being proximal to and immediately adjacent to said guiding mechanism, and in response to eversion of said eversible sleeve, said insertion tube's proximal end is pulled forward, and contemporaneously and in response to the forward advancement of said insertion tube, said eversible sleeve everts over the extended portion of said insertion tube's external surface and is pulled forward from said insertion tip;
   said telescoping tube assembly having a fully extended configuration such that said posterior tube's proximal end partially resides within said insertion tube's internal chamber, and said telescoping tube assembly having a fully retracted configuration wherein insertion tube is intended to be fully inserted within a body passageway and said eversible sleeve has unfurled to enclose said insertion tube's extended external surface, wherein said posterior tube's proximal end is distal relative to said insertion tube's proximal end when said telescoping tube assembly is in said fully retracted configuration; and
   said telescoping tube assembly can be withdrawn from a body passageway upon said posterior tube being distally pulled relative to said insertion tube, withdrawal of said posterior tube from said insertion tube causes said insertion tube to pull distally relative to the intended body passageway, and withdrawal of said insertion tube correspondingly causes said eversible sleeve to disengage and un-evert from the intended body lumen as it retracts back into said telescoping tube assembly.

2. The telescoping tube assembly of claim 1 further comprising a plurality of radial holes circumferentially surrounding said insertion tube's proximal end, a plurality of filaments or wires radially nesting within an inner wall of said telescoping tube assembly and extending longitudinally therethrough, said filaments or wires responsive to tensile force applied on said posterior tube's far distal wherein said filaments or wires cause insertion tube's far proximal end to bend proportionally and in the direction of the applied force.

3. The telescoping tube assembly of claim 1 further comprising swivel joints located on said external surface of said insertion tube's proximal end, a plurality of filaments or wires radially nesting within an inner wall of said telescoping tube assembly and extending longitudinally therethrough, said filaments or wires responsive to tensile force applied on said posterior tube's far distal wherein said filaments or wires cause insertion tube's far proximal end to bend proportionally and in the direction of the applied force.

4. The telescoping tube assembly of claim 1 further comprising a fluid collection bag attachment positioned at and removably affixed to said eversible sleeve's trailing end and said posterior tube's distal end; said fluid collection bag contiguous and in fluid connection with said hermetically sealed conduit.

5. The telescoping tube assembly of claim 1 wherein a sanitizing substance or antibacterial is applied to said eversible sleeve housed within said telescoping tube assembly so that the sanitizing substance or antibacterial can be applied to said sleeve as it unfurls into body lumen, thereby also applying such sanitizing substance or antibacterial to the internal walls of body lumen that are exposed to inserted said telescoping tube assembly.

6. The telescoping tube assembly of claim 1 wherein said guiding mechanism includes a fastener, wherein said fastener comprises a set screw or pin, and wherein said fastener is configured to threadably engage with said holding ring and said insertion tube.

7. The telescoping tube assembly of claim 1 wherein said insertion tube has a length equal to a length of said posterior tube, and wherein said eversible sleeve has a length equal to at least said insertion tube's length and said posterior tube's length.

* * * * *